United States Patent
Thorpe et al.

(10) Patent No.: US 11,596,380 B2
(45) Date of Patent: Mar. 7, 2023

(54) CATEGORIZATION OF WAVEFORM MORPHOLOGIES

(71) Applicant: NovaSignal Corp., Los Angeles, CA (US)

(72) Inventors: Samuel G. Thorpe, Los Angeles, CA (US); Corey M. Thibeault, Los Angeles, CA (US); Nicolas Canac, Los Angeles, CA (US); Kian Jalaleddini, Los Angeles, CA (US)

(73) Assignee: NovaSignal Corp., Los Angeles, CA (US)

( * ) Notice: Subject to any disclaimer, the term of this patent is extended or adjusted under 35 U.S.C. 154(b) by 20 days.

(21) Appl. No.: 16/792,169

(22) Filed: Feb. 14, 2020

(65) Prior Publication Data

US 2020/0261052 A1   Aug. 20, 2020

Related U.S. Application Data

(60) Provisional application No. 62/806,229, filed on Feb. 15, 2019.

(51) Int. Cl.
*A61B 8/08* (2006.01)
*A61B 8/06* (2006.01)

(52) U.S. Cl.
CPC .............. *A61B 8/0808* (2013.01); *A61B 8/06* (2013.01); *A61B 8/488* (2013.01)

(58) Field of Classification Search
CPC ......... A61B 8/0808; A61B 8/488; A61B 8/06; A61B 8/5223
See application file for complete search history.

(56) References Cited

U.S. PATENT DOCUMENTS

2005/0038342 A1* 2/2005 Mozayeni ............ A61B 8/0808
                                                          600/454
2014/0155788 A1   6/2014 Hoelscher et al.
(Continued)

FOREIGN PATENT DOCUMENTS

WO   WO-03/099131 A1   12/2003
WO   WO-2006/026548 A1   3/2006
(Continued)

OTHER PUBLICATIONS

Thorpe et al., "Decision Criteria for Large Vessel Occlusion Using Transcranial Doppler Waveform Morphology", Frontiers in Neurology vol. 9 (Oct. 17, 2018), p. 1-10 (Year: 2018).*
(Continued)

*Primary Examiner* — Joel Lamprecht
*Assistant Examiner* — Nyrobi Celestine
(74) *Attorney, Agent, or Firm* — Foley & Lardner LLP

(57) ABSTRACT

Arrangements described herein relate to systems, apparatuses, and methods for categorizing a waveform that includes processing a signal containing ultrasound data about the waveform, identifying one or more morphological variables of the waveform based on the ultrasound data, identifying one or more categories that correspond to a range of combinations of the morphological variables, and categorizing the waveform as belonging to one of the one or more categories. In some arrangements, the method may further include visualizing the waveforms, determining a probability that the waveform belongs to each of the one or more categories, and/or displaying the probability that the waveform falls into each of the one or more categories. Morphological variables may include quantifying absolute peak onset, number/prominence of auxiliary peaks, and systolic canopy length.

15 Claims, 10 Drawing Sheets

(56) References Cited

U.S. PATENT DOCUMENTS

| | | | |
|---|---|---|---|
| 2014/0357965 A1 | 12/2014 | Kashif et al. | |
| 2016/0256130 A1* | 9/2016 | Hamilton | A61B 8/06 |
| 2017/0188993 A1* | 7/2017 | Hamilton | A61B 8/4444 |
| 2018/0001114 A1 | 1/2018 | Li et al. | |
| 2018/0047553 A1* | 2/2018 | Richardson | A61B 5/0507 |
| 2019/0216433 A1* | 7/2019 | Hamilton | A61B 8/488 |

FOREIGN PATENT DOCUMENTS

| | | | | |
|---|---|---|---|---|
| WO | WO-2006026548 A1 * | 3/2006 | | A61B 5/378 |
| WO | WO-2006/067203 A1 | 6/2006 | | |

OTHER PUBLICATIONS

Demchuk et al., "Specific Transcranial Doppler Flow Findings Related to the Presence and Site of Arterial Occlusion", Stroke vol. 31 No. 1 (Jan. 2000), p. 140-146 (Year: 2000).*

Bathala et al. "Transcranial doppler: Technique and common findings (Part 1)", Ann Indian Acad Neurol. Apr. 2013; vol. 16 No. 2: p. 174-179. (Year: 2013).*

Hanlo et al., "Monitoring Intracranial Dynamics by Transcranial Doppler—A New Doppler Index: Transystolic Time", Ultrasound in Med. & Biol. vol. 21 No. 5 (1995), p. 613-621 (Year: 1995).*

Demchuk et al., "Thrombolysis in Brain Ischemia (TIBI) Transcranial Doppler Flow Grades Predict Clinical Severity, Early Recovery, and Mortality in Patients Treated With Intravenous Tissue Plasminogen Activator," Stroke, vo. 32, No. 1, pp. 89-93, Jan. 2001 (Year: 2001).*

International Preliminary Report on Patentability dated Aug. 26, 2021, from application No. PCT/US2020/018453.

International Search Report and Written Opinion dated Jun. 10, 2020, from application No. PCT/US2020/018453.

Naqvi, et al., "Transcranial Doppler Ultrasound: A Review of the Physical Principles and Major Applications in Critical Care", International Journal of Vascular Medicine, vol. 13, Article ID 629378, Nov. 10, 2013, 13 pages.

Thorpe, et al., "Decision Criteria for Large Vessel Occlusion Using Transcranial Doppler Waveform Morphology", Journal Frontiers in Neurology, Oct. 17, 2018, 11 pages.

Extended European Search Report dated Nov. 11, 2022, from application No. 20756736.3.

* cited by examiner

CATEGORIZATION OF WAVEFORM MORPHOLOGIES

CROSS-REFERENCE TO RELATED APPLICATIONS

This application claims the benefit of and priority to U.S. Provisional Patent Application No. 62/806,229, filed Feb. 15, 2019, the entire contents of which are incorporated herein by reference.

BACKGROUND

Transcranial Doppler ultrasound (TCD) is a noninvasive methodology for measuring Cerebral Blood Flow Velocity (CBFV) through the large arteries of the brain. The morphology of the pulsatile CBFV waveform can provide information concerning numerous cerebrovascular pathologies, including stroke, intracranial hypertension, and mild Traumatic Brain injury. TCD has proven effective for detecting occluded and stenosed cerebral arteries in the context of acute ischemic stroke. Additionally, CFBV waveforms acquired via TCD can provide evidence for cerebrovascular occlusion and stenosis. Thrombolysis in Brain Ischemia (TIBI) flow grades are widely used for this purpose but require subjective assessment by expert evaluators to be reliable. However, reliable determination of TIBI grades uses subjective assessment by experts, severely limiting the utility for prehospital stroke assessment by less specialized personnel.

SUMMARY

In some arrangements, a method of categorizing a waveform includes processing a signal containing ultrasound data about the waveform, identifying one or more morphological variables of the waveform based on the ultrasound data, identifying one or more categories that correspond to a range of combinations of the morphological variables, and categorizing the waveform as belonging to one of the one or more categories.

In some arrangements, the method further includes visualizing the one or more categories.

In some arrangements, the method categorizes the waveform as belonging to the one of the one or more categories by determining a probability that the waveform belongs to the one or more categories, and visualizes the one or more categories by displaying the probability.

In some arrangements, the one or more morphological variables include a first variable including an absolute peak onset of the waveform, a second variable including a length of a canopy of the waveform, and a third variable including one or more of a number of one or more auxiliary peaks of the waveform or prominence of the one or more auxiliary peaks of the waveform.

In some arrangements, visualizing the one or more categories includes mapping the first variable along a first axis, the second variable along a second axis, and the third variable along a third axis. In some arrangements, the first axis, the second axis, and the third axis are different axes.

In some arrangements, each of the one or more categories corresponds to a designated area within a three-dimensional space defined by the first axis, the second axis, and the third axis.

In some arrangements, the first variable is categorized as early or late, the second variable is categorized as wide or narrow, and the third variable is categorized as weak or strong.

In some arrangements, the waveform is categorized as being in the first category in response to determining that the first variable is categorized as late, the second variable is categorized as wide, and the third variable is categorized as strong.

In some arrangements, the waveform is categorized as being in the second category in response to determining that the first variable is categorized as late, the second variable is categorized as wide, and the third variable is categorized as strong.

In some arrangements, the waveform is categorized as being in the third category in response to determining that the first variable is categorized as early, the second variable is categorized as narrow, and the third variable is categorized as weak.

In some arrangements, the waveform is categorized as being in the fourth category in response to determining that the first variable is categorized as late, the second variable is categorized as wide, and the third variable is categorized as weak.

In some arrangements, the waveform corresponds to blood flow within one or more cerebral arteries of the subject and the first category corresponds to the blood flow through the one or more cerebral arteries being normal, the third category corresponds to the blood flow through the one or more cerebral arteries being occluded, and the fourth category corresponds to the blood flow through the one or more cerebral arteries being blunted.

In some arrangements, the designated areas of two or more categories overlap.

In some arrangements, the waveform corresponds to blood flow of a subject.

In some arrangements, the blood flow includes blood flow within one or more cerebral arteries of the subject.

In some arrangements, the one or more categories correspond to one or more pathologies of the subject.

In some arrangements, one of the one or more pathologies may be one or more of stroke, intracranial hypertension, and mild traumatic brain injury.

In some arrangements, the one or more categories include four categories that correspond to previously known TIM flows.

In some arrangements, a TCD transducer collects the ultrasound data and identifies the one or more morphological features of the waveform.

In some arrangements, an automated algorithm is instructed to perform the method.

In some arrangements, a method of visualizing waveforms of blood flow of a subject includes collecting data about a waveform using ultrasound insonation, automatically identifying one or more morphological variables of the waveform from the data, automatically referencing one or more predetermined categories that correspond to a range of combinations of the morphological variables, automatically determining a probability that the waveform belongs to each of the one or more categories, categorizing the waveform as belonging to one of the one or more categories, displaying the one of the one or more categories, and indicating the probability that the waveform falls into each of the one or more categories.

In some arrangements, a first variable of the one or more morphological variables is an absolute peak onset of the waveform, a second variable of the one or more morphological variables is a length of a canopy of the waveform, and a third variable of the one or more morphological variables is one of a number or prominence of an auxiliary peak of the waveform.

In some arrangements, a device for visualizing categorization of a waveform includes a probe, a processing circuit, and a display. The probe may collect data from the waveform. The processing circuit may identify one or more morphological variables of the waveform from the data, references one or more predetermined categories that correspond to a range of combinations of the morphological variables, determine a probability that the waveform belongs to each of the one or more predetermined categories, and categorize the waveform as belonging to one of the one or more predetermined categories. The display may display the one of the one or more predetermined categories and the probability determined by the processing circuit.

BRIEF DESCRIPTION OF THE FIGURES

Features and aspects of the present disclosure will become apparent from the following description and the accompanying example arrangements shown in the drawings, which are briefly described below.

DETAILED DESCRIPTION

Figure 1:
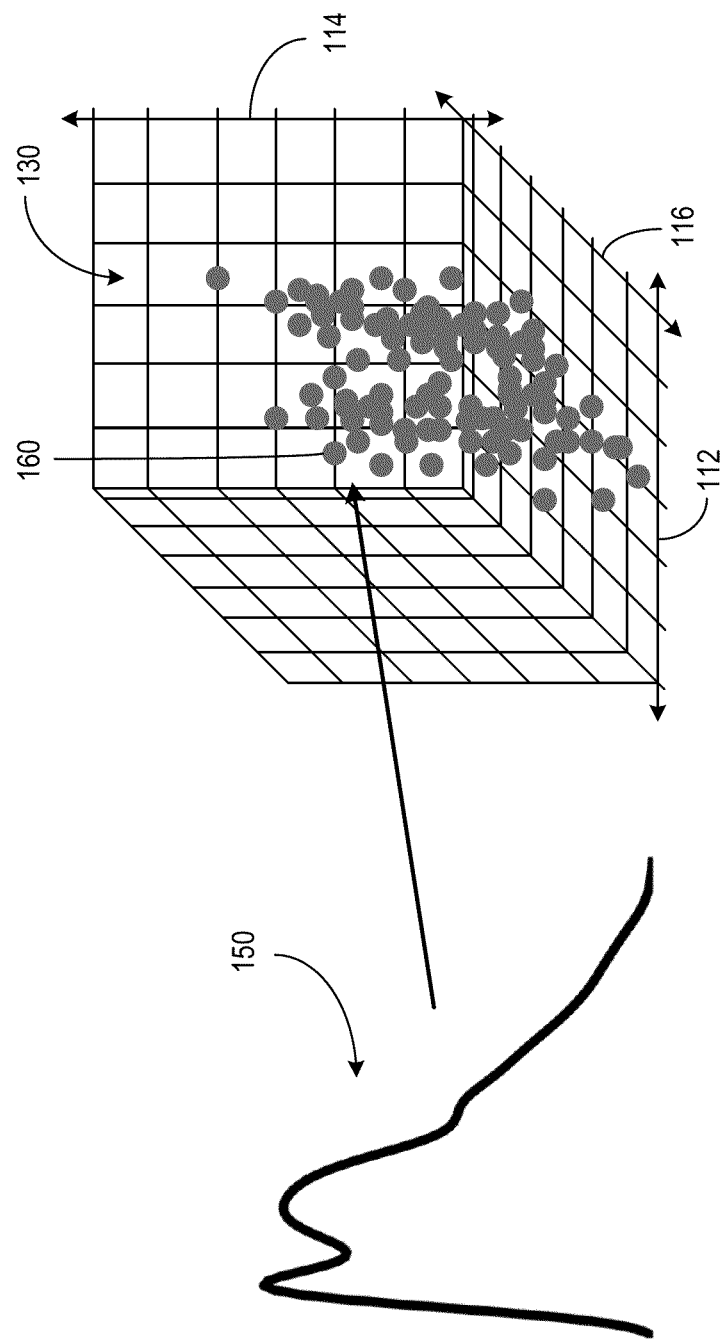
FIG. 1 depicts visualization of a single waveform translated into a three-dimensional representation, according to various arrangements.

The detailed description set forth below in connection with the appended drawings is intended as a description of various configurations and is not intended to represent the only configurations in which the concepts described herein may be practiced. The detailed description includes specific details for providing a thorough understanding of various concepts. However, it will be apparent to those skilled in the art that these concepts may be practiced without these specific details.

In the following description of various arrangements, reference is made to the accompanying drawings which form a part hereof and in which are shown, by way of illustration, specific arrangements in which the arrangements may be practiced. It is to be understood that other arrangements may be utilized, and structural changes may be made without departing from the scope of the various arrangements disclosed in the present disclosure Systems and methods for automated flow type classification are described herein, including identifying one or more variables of a waveform, categorizing clusters according to trends in the one or more variables, and matching the identified clusters to known pathological presentations.

Systems, methods, and apparatuses for objective assessment of TCD morphology using a machine learning approach to categorize waveforms are herein described. According to various arrangements, pathological TCD waveform morphology is automatically categorized via spectral clustering. In some arrangements, one or more morphological variables may be extracted from each waveform. Examples of the variables include but are not limited to, quantified absolute peak onset, a number/prominence of auxiliary peaks, systolic canopy length, and so on. In some arrangements, spectral clustering may be used to identify groups implicit in the resultant three-dimensional feature space, with gap-statistic maximization identifying the optimal number of clusters. In some arrangements, TCD morphological variability exists beyond that currently quantified by TIBI flow grades in populations experiencing or at-risk for acute ischemic stroke. In some arrangements, spectral clustering and the morphological archetypes described herein may provide the foundation for objective methods of real-time automated flow type classification. The collection of data from a pulsatile flow that results in a waveform may be referred to as a beat.

In various arrangements herein disclosed, stroke pathology is primarily quantified using Thrombolysis in Brain Ischemia (TIBI) flow grades to evaluate waveform morphology. However, reliable determination of TIBI grades traditionally employ subjective assessment by experts, thus severely limiting utility for prehospital stroke assessment by less specialized personnel. In some arrangements, a TCD-derived morphological biomarker termed Velocity Curvature Index (VCI) may provide a robust, objectively computable metric for detecting Large Vessel Occlusion (LVO). Though VCI readily identifies waveforms with pathologically deviant curvature, VCI does not differentiate between pathological morphologies such as those delineated by the TIBI scale. In some arrangements, an objective waveform categorization provides additional information concerning stroke etiology to better inform stroke triage and transfer decisions. In some arrangements, Type I and II clusters may be primarily composed of waveforms indicative of control patient populations, whereas Type III and IV clusters may be primarily correlated with LVO patient waveforms.

In some arrangements, a data-driven approach to waveform categorization may be taken, retrospectively applying an unsupervised learning algorithm to a dataset including multiple subject groups. The subject groups include patients experiencing acute LVO, as well as control subjects collected both in and out of hospital. In some arrangements, spectral clustering may be employed. Spectral clustering does not make strong assumptions about inherent cluster density, and thus performs well when clusters are connected but non-convex. In some arrangements, LVO subject waveforms fall into clusters which are mostly distinct from non-LVO controls, and subsequently the observed clusters with established TIBI categories are compared.

In some arrangements, TCD waveform morphology may be compared across three subject groups: one with CTA-confirmed LVO, a second non-LVO control group collected in-hospital, and a third group of control subjects collected out of hospital (OHC). LVO and in-hospital controls (IHC) were enrolled.

In some arrangements, CBFV signals may be acquired using ultrasound probes (e.g., 2 MHz probes) or transducers to trans-temporally insonate the left/right MCA. In some arrangements, this signal is acquired by an automated process, for instance by a programmed ultrasound transducer. In some arrangements, recordings may be obtained for as many depths as possible between 45-60 mm in both the left/right cerebral hemispheres. In some arrangements, once signal is identified and optimized at a specific depth, waveform recordings may be made in 30-second intervals. Individual beat waveforms from each recorded depth may be extracted offline (post-recording) using an automated beat identification algorithm, with automated beat outlier rejection via Iterated Interquartile Range exclusion with cross-correlation and beat length as primary comparators. In some arrangements, exams may contain at least one bilateral pair of left/right MCA scans at depths between 45-60 mm, each containing at least 15 accepted beats. In some arrangements, accepted beats may be aligned and averaged, resulting in a single representative beat waveform for each recorded interval. In some arrangements, OHC waveforms, digitally sampled at 400 Hz, may be resampled to 125 Hz to match the native sampling rate of LVO and IHC waveforms. In some arrangements, waveforms may be smoothed via convolution with a 9 ms Hanning window to reduce high-frequency noise. Since some arrangements herein described evaluate morphological commonality regardless of underlying heart rate or velocity scale, each waveform may be normalized with respect to both time and velocity. In some arrangements, velocity normalization may be accomplished for each waveform by first subtracting the minimum, then subsequently dividing by the resultant maximum (thus rescaling to the interval [0, 1] along the velocity axis). In some arrangements, the temporal normalization may be accomplished by resampling each waveform to 100 total samples (via cubic spline), effectively enforcing a common heart rate across waveforms.

In some arrangements, three morphological features may be extracted from each waveform, denoted x(t) in equations (1)-(3), quantifying absolute peak onset, systolic canopy length, and number/prominence of auxiliary peaks, respectively. The first, onset (defined in equation (1)), may mark the temporal onset of maximal velocity. The second, canopy (defined in equation (2)), may indicate the number of samples including the beat "canopy". The final feature, peaks (defined in equation (3)), may quantify the number and "weight" of waveform peaks.

$$\text{onset} = n : x(t_n) = \max_{i \in \{1,2,\ldots 100\}} \{x(t_i)\}; \quad (1)$$

$$\text{canopy} = \text{card}(\{i : x(t_i) > x(t_0) + 0.25(x(t_{systolic}) - x(t_{diastolic}))\}); \quad (2)$$

$$\text{peaks} = \text{card}(TP) + \sum_{k \in PP} 1 - \frac{|x(t_k) - x(t_{k-1})|}{0.01} \quad (3)$$

Spectral clustering may be used to identify groups implicit in the resultant three-dimensional feature space, with gap-statistic criteria identifying the optimal number of clusters. Beat archetypes for each resultant cluster are derived in some arrangements as the average of the five cluster examples with smallest mean correlation distance across cluster members. Waveforms may be normalized in both time and velocity, so that any samples included range from zero to one on the y-axis. The onset variable marks the time sample where maximum velocity is attained, as plotted on a normalized x-axis. In various arrangements, the onset variable may occur after about the 20% mark of the normalized x-axis, in some of these arrangements, the onset may be categorized as "late." In some of these arrangements, the onset variable may occur before about 20% of the normalized x-axis and be categorized as "early." Although 20% may be recognized in some arrangements as an example threshold, the definition between late and early may be designated as any point along the normalized axis. The canopy variable marks the length (in samples) of the systolic canopy. This length may be measured as occurring over a stretch of the x-axis. In various arrangements, the canopy variable may stretch across approximately 50% or more of the x-axis, and in some arrangements, the canopy variable may be categorized as "wide" when it stretches across more than 50% of the length of the x-axis. In various arrangements, the canopy variable length may stretch across less than 50% of the x-axis and in some arrangements may be categorized as "narrow." Although 50% may be recognized in some arrangements as an example threshold, the definition between a wide and narrow canopy could be any percentage of length spanned over the x-axis. The peaks variable is a weighted sum of waveform peaks, both true and pseudo.

In some arrangements, a set of true-peaks (TP, approximate zeros of the first derivative) may be identified as points in the canopy corresponding to a sign-change in the difference between successive samples. True peaks may each be assigned a weight of one. In some arrangements, a set of "pseudo-peaks" (PP, points where the derivative is small but non-vanishing) where the difference magnitude between successive samples dropped below a critical threshold of 0.01 (choosing the point with smallest difference magnitude in any group of adjacent sub-threshold samples) may be identified. In some arrangements, weights corresponding to one minus the ratio of the associated difference magnitude and the threshold 0.01, such that those with the smallest derivative were weighted most heavily may be assigned to pseudo-peaks. For pseudo-peaks, the peaks may be assigned a variable which may then be computed as the sum over all corresponding weights. When this sum is above a threshold of approximately 4 peaks, the peaks may be categorized as "strong." Below a threshold of about 4 peaks, the peaks may be categorized as "weak." Although 4 peaks is indicated as a representative threshold in some arrangements, any number to a person highly skilled in the art could be selected as a threshold.

The waveforms described herein are determined based on ultrasound data collected by an ultrasound probe (transducer). For example, based on output of the probe, blood flow velocity signals can be generated. The blood flow velocity signal is continuous in the time-domain. A waveform is segmented from the continuous blood flow velocity signal. Each waveform is illustrated in a graph representing blood flow velocity (e.g., in cm/s or cm/ms) against time (in s or ms).

FIG. 1 depicts a waveform 150 that is translated into a three-dimensional representation thereof, according to some arrangements. Referring to FIG. 1, the waveform 150 is translated (mapped) to a point 160 within a space 130 that is defined by a first axis 112, a second axis, 114, and a third axis 116. The first axis 112 corresponds to a first morphological variable, such as but not limited to, an onset variable that identifies the time at which a maximum velocity of the waveform 150 occurs. The second axis 114 corresponds to a second morphological variable, such as but not limited to, a canopy variable that identifies a length of a canopy of the waveform 150. The third axis 116 corresponds to a third morphological variable, such as but not limited to, a peaks variable that is a weighted sum of peaks of the waveform 150. In other words, the morphological variables are extracted from the waveform 150 and mapped to the point 160 in the space 130 by plotting the extracted morphological variables along the axes 112, 114, and 116. As shown, the space 130 contains multiple points, each of which represents a waveform. Each of the points in the space 130 is determined for a corresponding waveform in the manner that the point 160 is determined for the waveform 150. In some examples, the space 130 and the points (e.g., the point 160) therein are displayed using a suitable display device to a user. In some examples, one or more waveforms (e.g., the waveform 150) are also displayed using the display device to the user, along with the space 130 and the corresponding points (e.g., the point 160).

Figure 2:
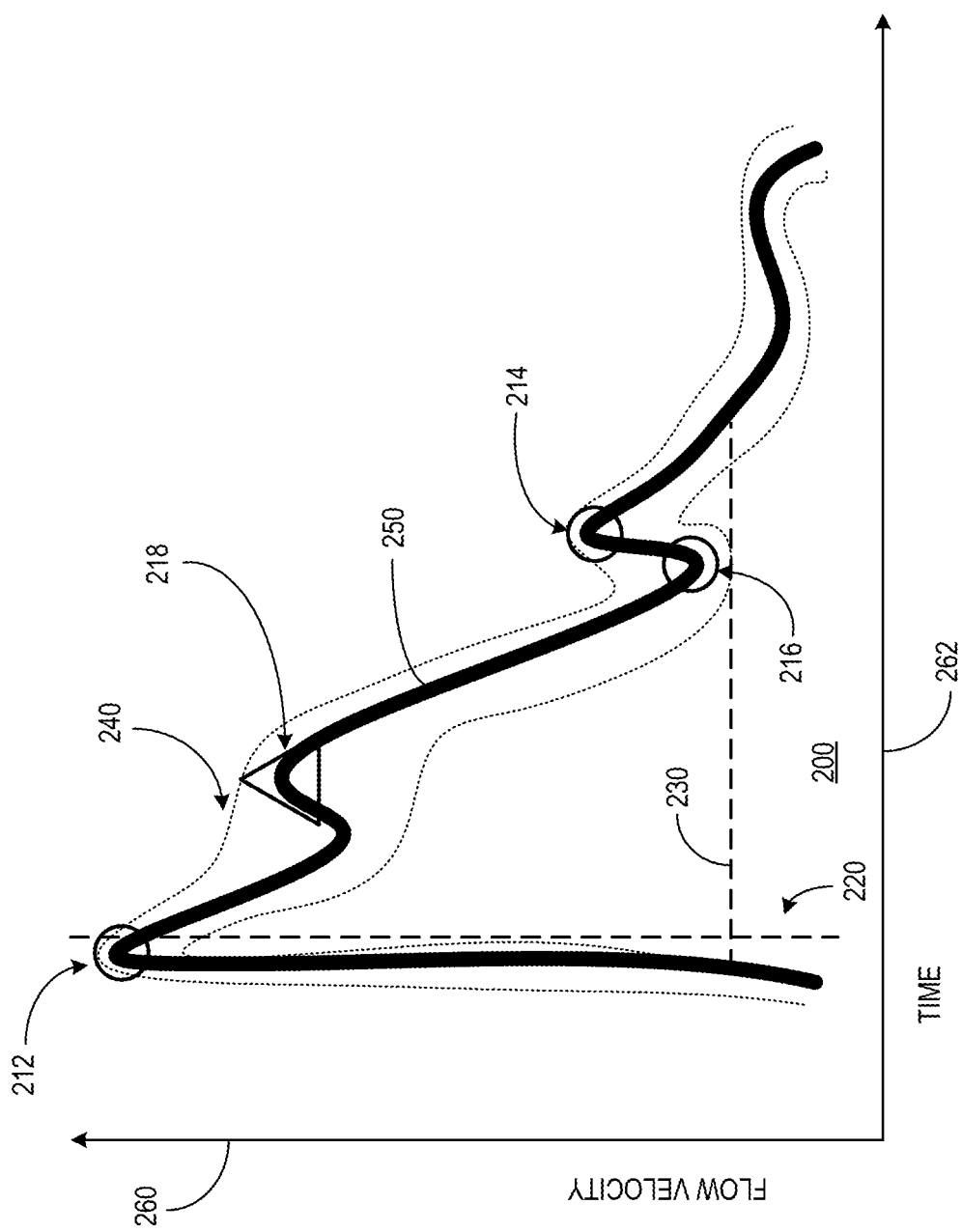
FIG. 2 depicts a waveform with various morphological features, according to various arrangements.

FIG. 2 depicts waveform data 200 with various morphological features, according to various arrangements. Referring to FIGS. 1-2, the waveform data 200 corresponds to the blood flow velocity signals illustrated as blood flow velocity 260 (vertical, y-axis) against time 262 (horizontal x-axis). In some arrangements, the waveform data 200 includes multiple samples 240 (corresponding to multiple possible waveforms) that can be aggregated and/or normalized to obtain an representative waveform 250 of the subject. The samples 240 of the waveform data 200 are shown as the shaded region around the representative waveform 250. Various morphological features can be identified for the representative waveform 250. Examples of the morphological features include but are not limited to, an onset of the representative waveform 250, a length of a canopy of the representative waveform 250, a peaks variable of the representative waveform 250, and so on.

As shown, an onset variable 220 marks (identifies) the time at which maximum velocity of the representative waveform 250 occurs. In addition, an canopy variable 230 marks (identifies) a length of the canopy of the representative waveform 250. The peaks variable is a weighted sum of waveform peaks, for all of true peaks 212, 214, and 216 and a pseudo peak 218. Each of the true peaks 212, 214, and 216 includes a minimum or maximum, both absolute and relative. The pseudo peak 218 includes any other point of inflection. Other representative waveforms can be similarly determined based on corresponding waveform data and samples thereof, and the morphological features of those representative waveforms can be similarly determined and marked.

Figure 3A:
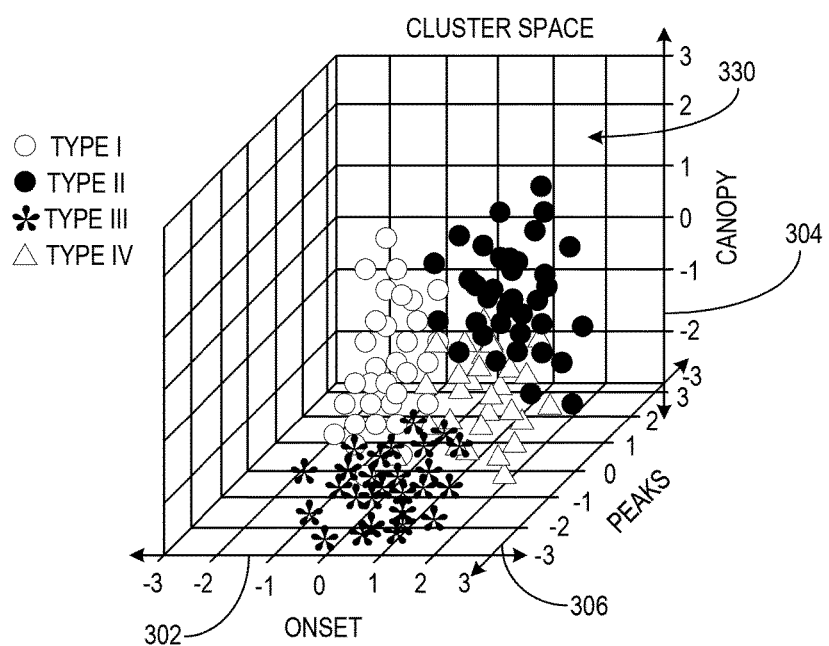
FIG. 3A shows a three-dimensional cluster space with clusters, according to various arrangements.

FIG. 3A shows a three-dimensional cluster space 330 with clusters, according to various arrangements. Referring to FIGS. 1-3A, the cluster space 330 is defined by a first axis 302, a second axis, 304, and a third axis 306. The first axis 302 corresponds to a first morphological variable, such as but not limited to, an onset variable that identifies the time at which a maximum velocity of each waveform occurs. The second axis 304 corresponds to a second morphological variable, such as but not limited to, a canopy variable that identifies a length of a canopy of each waveform. The third axis 306 corresponds to a third morphological variable, such as but not limited to, a peaks variable that is a weighted sum of peaks of each waveform. Each point in the cluster space 330 represents a different waveform, in the manner described.

The points in the cluster space 330 form clusters. For example, spectral clustering can be used to identify groups of points implicit in the cluster space 330, which is a three-dimensional feature space. Gap-statistic maximization can be used to identify an optimal number of clusters. In the example shown in FIG. 3A, gap-statistic disparity can be maximized at four clusters, referred to herein as a flow type I cluster (category one cluster 312), a flow type II cluster (category two cluster 314), a flow type III cluster (category three cluster 316), and a flow type IV cluster (category four cluster 318). Points in the cluster 312 are denoted as "○" in the cluster space 330. Points in the cluster 314 are denoted as "⊙" in the cluster space 330. Points in the cluster 316 are denoted as "*" in the cluster space 330. Points in the cluster 318 are denoted as "Δ" in the cluster space 330.

In some arrangements, archetypes for two clusters (e.g., clusters 312 and 318) displayed morphologies readily classifiable as unique TIBI flow grades. For example, the clusters 312 and 318 (the waveforms corresponding to points thereof) corresponding to Normal (grade 5) and Blunted (grade 2) flows, respectively. In some arrangements, clusters 314 and 316 (the waveforms corresponding to points thereof) represent commonly observed flow-types not delineated by the TIBI scale, which may nonetheless deviate quantifiably from normal and blunted waveforms. In some arrangements, the cluster 314, along with the normal cluster 312, may primarily be composed of waveforms from control patient populations, whereas the 314 cluster, along with the blunted cluster 318, may be composed mainly of LVO patient waveforms.

In some arrangements, the extracted features (defined by the morphological variables as described) can be z-transformed, and the resultant three-dimensional feature space 330 can be partitioned via spectral clustering. Default parameters and radial basis kernel can be applied. In some arrangements, one or more archetypal waveforms in each of the clusters 312, 314, 316, 318 can be derived for each of the resultant clusters 312, 314, 316, 318 by computing a matrix of correlation distances between all cluster member waveforms and ranking by average distance to other members, to visualize the characteristic morphologies of the resultant clusters 312, 314, 316, 318. In some arrangements, five waveforms with smallest mean intra-cluster distances may be averaged to obtain the archetypal waveform for each of the clusters 312, 314, 316, 318. Accordingly, the associated feature space 330 is shown to be partitioned into the four resultant clusters 312, 314, 316, 318.

Figures 3B, 3C, 3D, 3E:
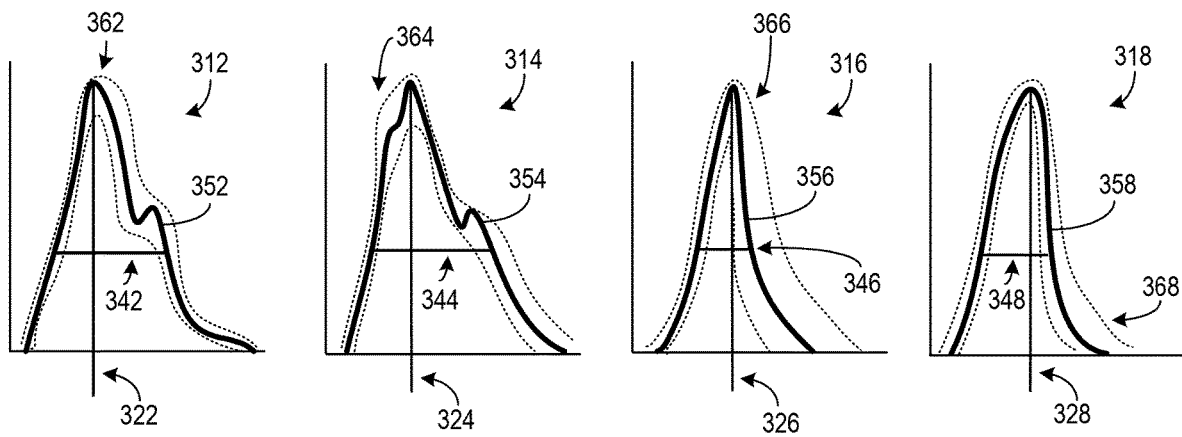
FIG. 3B depicts cluster morphologies of waveforms categorized in a first category, according to various arrangements.
FIG. 3C depicts cluster morphologies of waveforms categorized in a second category, according to various arrangements.
FIG. 3D depicts cluster morphologies of waveforms categorized in a third category, according to various arrangements.
FIG. 3E depicts cluster morphologies of waveforms categorized in a fourth category, according to various arrangements.

FIG. 3B depicts cluster morphologies of waveforms categorized in a first category (category one), according to various arrangements. Referring to FIGS. 1-3B, the first category corresponds to the cluster 312. The points shown in the cluster space 330 that belong to the cluster 312 are represented by waveform data corresponding to multiple samples 362 (corresponding to multiple waveforms). The samples 362 are aggregated and/or normalized to obtain an representative waveform 352. Features of the representative waveform 352, such as but not limited to, a max velocity onset 322, a canopy 342, and peaks, can be identified in the manner described herein. As shown, waveforms in the cluster 312 can be characterized by the earlier max velocity onset 322 and the wider canopy 342, with strong, distinguishable (identifiable) peaks.

FIG. 3C depicts cluster morphologies of waveforms categorized in a second category (category two), according to various arrangements. Referring to FIGS. 1-3C, the second category corresponds to the cluster 314. The points shown in the cluster space 330 that belong to the cluster 314 are represented by waveform data corresponding to multiple samples 364 (corresponding to multiple waveforms). The samples 364 are aggregated and/or normalized to obtain an representative waveform 354. Features of the representative waveform 354, such as but not limited to, a max velocity onset 324, a canopy 344, and peaks, can be identified in the manner described herein. As shown, waveforms in the cluster 314 can be characterized by the later max velocity onset 324 and the wider canopy 344, with strong, distinguishable (identifiable) peaks.

FIG. 3D depicts cluster morphologies of waveforms categorized in a third category (category three), according to various arrangements. Referring to FIGS. 1-3D, the third category corresponds to the cluster 316. The points shown in the cluster space 330 that belong to the cluster 316 are represented by waveform data corresponding to multiple samples 366 (corresponding to multiple waveforms). The samples 366 are aggregated and/or normalized to obtain an representative waveform 356. Features of the representative waveform 356, such as but not limited to, a max velocity onset 326, a canopy 346, and peaks, can be identified in the manner described herein. As shown, waveforms in the cluster 314 can be characterized by the earlier max velocity onset 326 and the narrower canopy 346, with weak, indistinguishable (unidentifiable) peaks.

FIG. 3E depicts cluster morphologies of waveforms categorized in a fourth category (category four), according to various arrangements. Referring to FIGS. 1-3E, the fourth category corresponds to the cluster 318. The points shown in the cluster space 330 that belong to the cluster 318 are represented by waveform data corresponding to multiple samples 368 (corresponding to multiple waveforms). The samples 368 are aggregated and/or normalized to obtain an representative waveform 358. Features of the representative waveform 358, such as but not limited to, a max velocity onset 328, a canopy 348, and peaks, can be identified in the manner described herein. As shown, waveforms in the cluster 318 can be characterized by the later max velocity onset 328 and the wider canopy 328, with weak, indistinguishable (unidentifiable) peaks.

Figure 4:
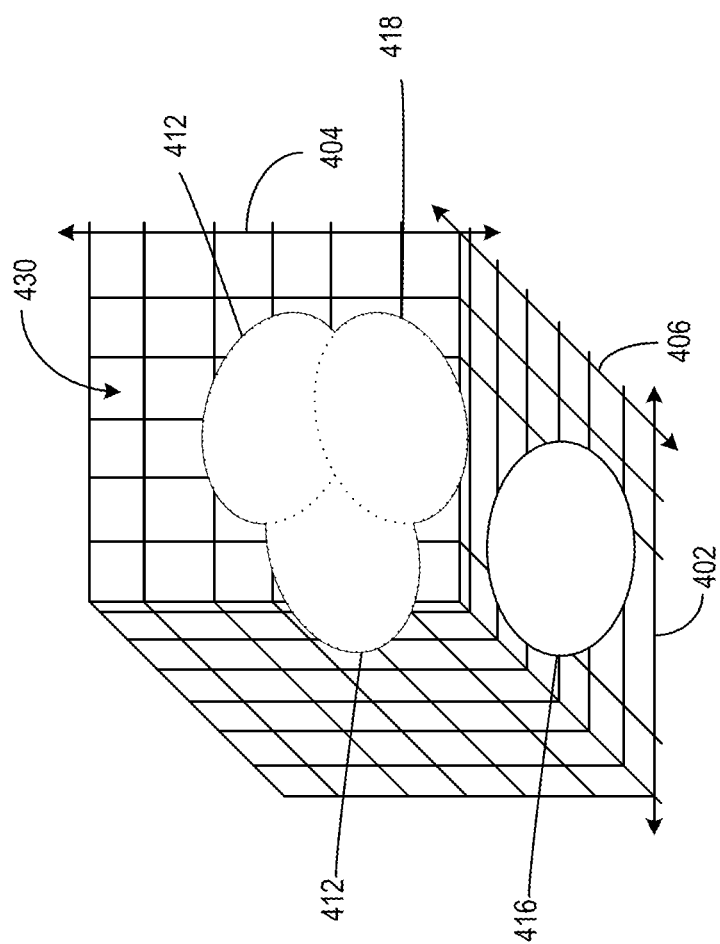
FIG. 4 depicts categories (clusters) of waveforms that correspond to volumes within a three-dimensional space, according to various arrangements.

FIG. 4 depicts categories (clusters) of waveforms that correspond to volumes within a three-dimensional cluster space 430, according to various arrangements. Referring to FIGS. 1-4, the 3-dimensional cluster space 430 is defined by a first axis 402, a second axis 404, and a third axis 406. The first axis 402 corresponds to a first morphological variable, such as but not limited to, an onset variable that identifies the time at which a maximum velocity of each waveform occurs. The second axis 404 corresponds to a second morphological variable, such as but not limited to, a canopy variable that identifies a length of a canopy of each waveform. The third axis 406 corresponds to a third morphological variable, such as but not limited to, a peaks variable that is a weighted sum of peaks of each waveform. Each point (not shown) in the cluster space 430 represents a different waveform, in the manner described. The points in the cluster space 430 form clusters (e.g., clusters 412, 414, 416, and 418), in the manner described herein. Points (not shown) populate within boundaries of each the clusters 412, 414, 416, and 418.

As shown, adjacent clusters 412 and 418 share a fuzzy boundary (having indistinguishable boundaries such that it is uncertain whether some of the points belong to the cluster 412 or 418, or the adjacent clusters 412 and 418 overlap) primarily determined by the peaks variable (axis 406), suggesting the clusters 412 and 418 can be difficult to differentiate when systolic peaks are not clear, e.g., when the systolic peaks are weak, indistinguishable (unidentifiable). In various arrangements, the cluster 418 may have the least homogenous group composition, with approximately 40% of waveforms originating from control subjects. This may negatively impact specificity to use these clusters alone to classify LVO in some cases. As described herein, further processing can be applied for additional or refined clustering features that can disambiguate clusters that share a fuzzy boundary.

Figure 5A:
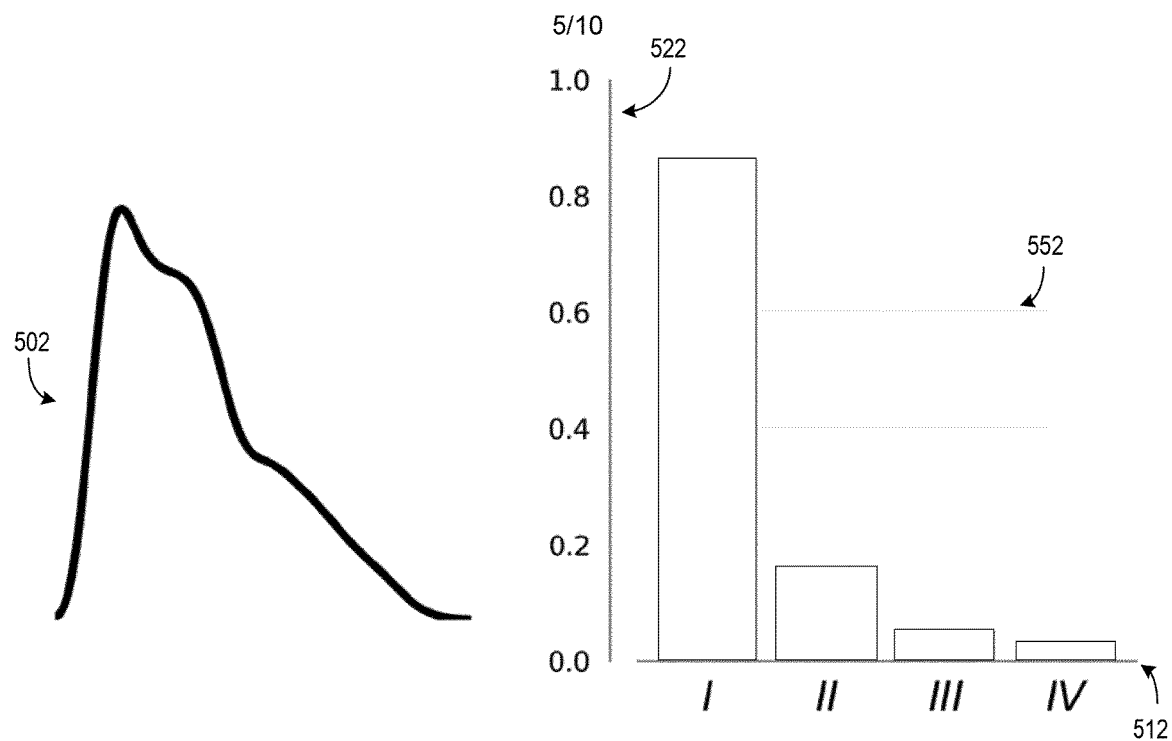
FIGS. 5A and 5B each depicts a waveform and an associated histogram displaying the probability that the waveform fits into various categories, according to various arrangements.
Figure 5B:
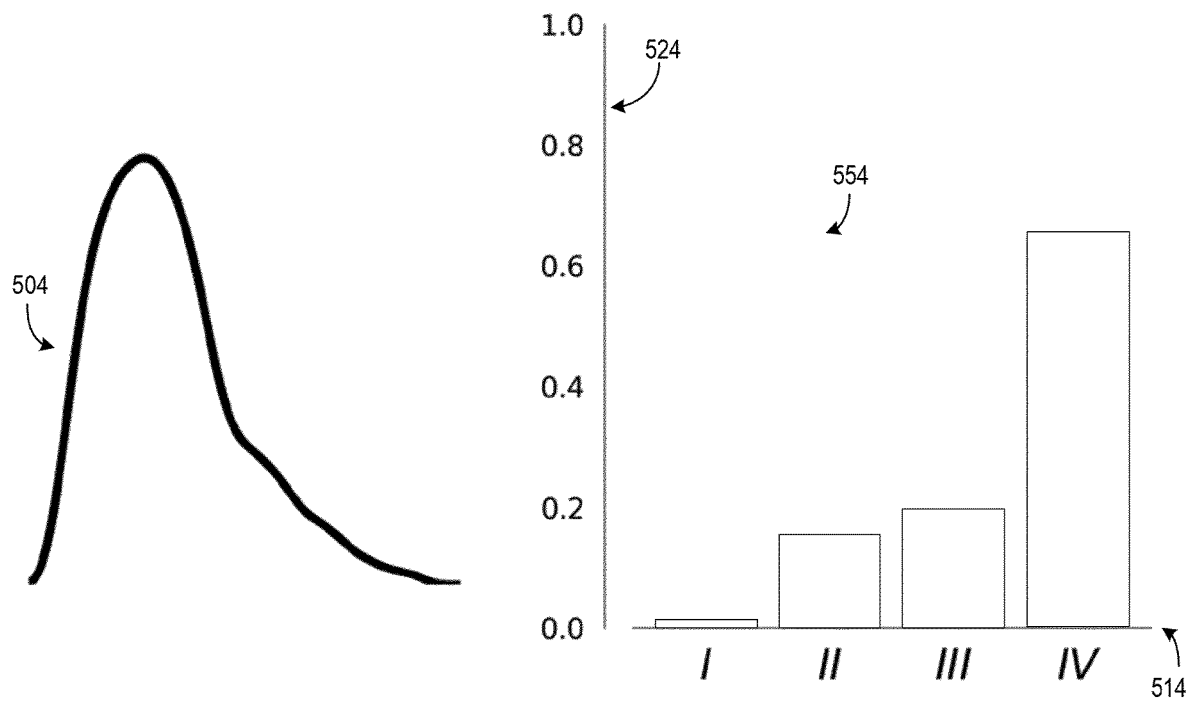

FIGS. 5A and 5B each depicts a waveform 502 or 504 and an associated histogram 552 or 554, respectively, that displays the probability that the waveform 502 or 504 fits into various categories, according to various arrangements. Referring to FIGS. 1-5B, the waveform 502 belongs category one as described herein. A first histogram 552 depicts the probability on a vertical, y-axis 522 versus of different possible categories (categories one to four or Types I-IV) on the horizontal, x-axis 512. As shown, the waveform 502 has a high probability of being in category one (type I). The waveform 504 belongs category four as described herein. A second histogram 554 depicts the probability on a vertical, y-axis 524 versus of different possible categories (categories one to four or Types I-IV) on the horizontal, x-axis 514. As shown, the waveform 504 has a high probability of being in category four (type IV).

Figure 6:
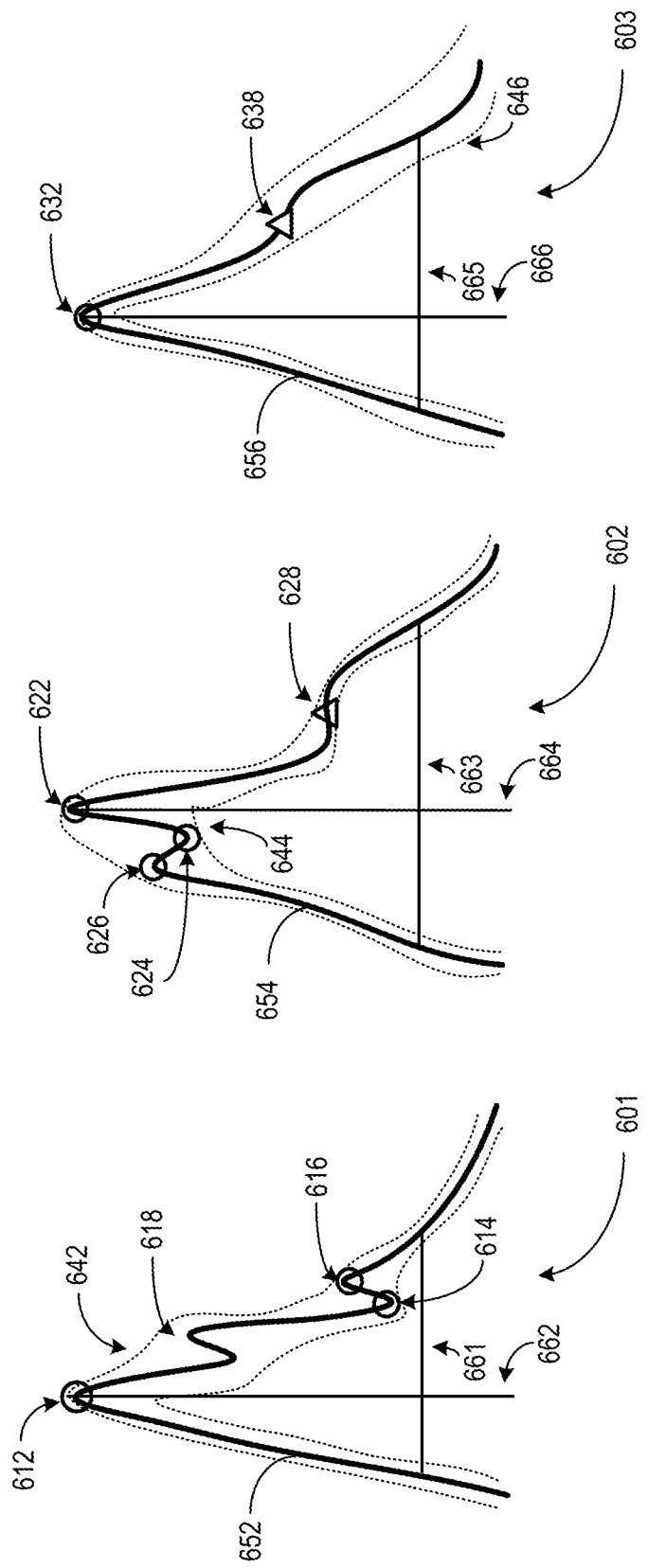
FIG. 6 depicts various waveforms with different morphological features represented by different combinations of morphological variables, according to various arrangements.

FIG. 6 depicts various waveforms 601, 602, and 603 with different morphological features represented by different combinations of morphological variables, according to various arrangements. Referring to FIGS. 1-6, various permutations of the morphological variables in various arrangements are depicted. In the waveforms 601 (category one), a representative waveform 652 can be computed by aggregating and/or normalizing waveform data corresponding to multiple samples 642 (corresponding to the multiple waveforms 601). The waveform 601 can be characterized as having an earlier peak onset 662, a wider canopy 661, and strong, distinguishable (identifiable) peaks 612, 614, 616, 618. In various arrangements, the waveforms 601 may correspond to an output determined for a hospital control group.

In the waveforms 602 (category two), a representative waveform 654 can be computed by aggregating and/or normalizing waveform data corresponding to multiple samples 644 (corresponding to the multiple waveforms 602). The representative waveform 654 can be characterized as having a later peak onset 664, a wider canopy 663, and strong, distinguishable (identifiable) peaks 622, 624, 626, 628. In various arrangements, the waveforms 602 may correspond to output determined for an in-hospital control group. The pronounced differences between the waveform 601s and the waveforms 602 include that the first-category peak onset 662 is closer to a left portion the representative waveform 652, whereas the second-category peak onset 664 is farther from a left portion of the representative waveform 654, differentiating an early peak from a late peak.

In the waveforms 603 (category three), a representative waveform 656 can be computed by aggregating and/or normalizing waveform data corresponding to multiple samples 646 (corresponding to the multiple waveforms 603). The representative waveform 656 can be characterized as having a later peak onset 666, a wider canopy 665, and weak, indistinguishable (unidentifiable) peaks 632 and 638. In various arrangements, the waveforms 603 may correspond to outputs determined for a group experiencing LVO. Compared to the first-category waveforms 601 and second-category waveforms 602, the third-category waveforms 603 have fewer peaks (e.g., two peaks, the peaks 632, 638) as opposed to the first-category's four peaks 612, 614, 616, 618 and the second category's four peaks 622, 624, 626, 628, differentiating waveforms 603 with weak peaks from waveforms 601 and 602 with strong peaks.

Figure 7:
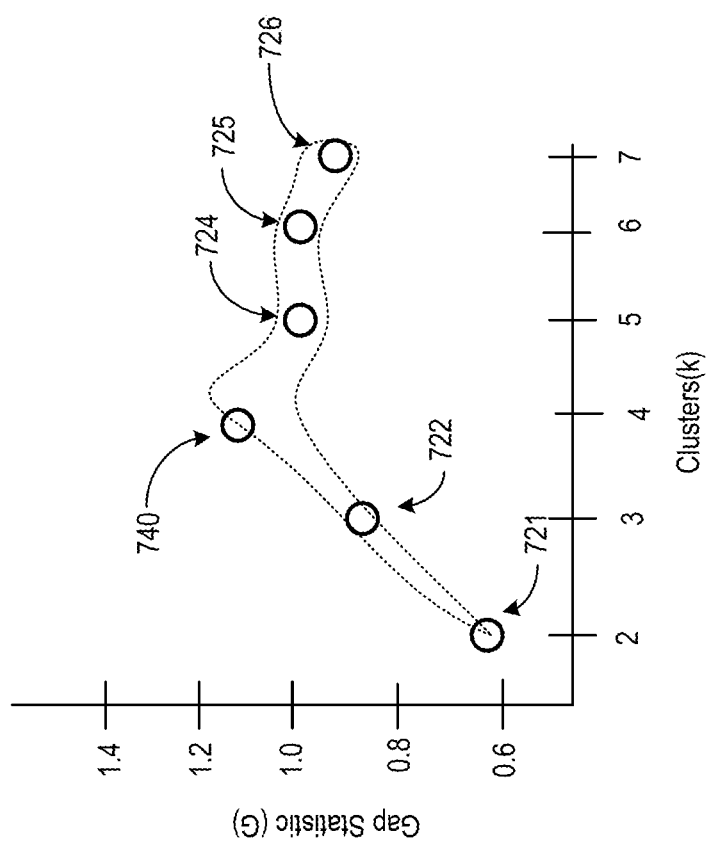
FIG. 7 is a graph depicting Gap-statistic disparity for clusters, according to various arrangements.

FIG. 7 depicts Gap-statistic disparity for clusters, according to various arrangements. Referring to FIGS. 1-7, to determine the optimal number of clusters, gap statistics ($G_k$) may be computed for total clusters (k), including clusters 721, 722, 723, 724, 725, and 726. In some arrangements, gap statistics may be computed as the difference between observed log intra-cluster dispersion pooled across k clusters (denoted $W_k$). The analogous expected dispersion bootstrapped from a null distribution incorporating the covariance structure of the observed data. Each bootstrap iteration can be generated by sampling uniformly over the range of the columns of the observed data transformed by its right-singular vectors, and back-transforming the resultant samples to a feature space via the right-singular transpose. In some arrangements, the number of clusters may be selected as the smallest k such that $G_k > G_{k+1} - S_{k+1}$, where Sk is the standard deviation of the k-cluster bootstrap distribution corrected to account for simulation error. The elbow 740 in observed dispersion at four clusters corresponds to both the maximum gap statistic and determined optimal number of clusters.

In the various arrangements herein disclosed, identified clusters have definitive analogues on the TIBI scale. In some arrangements, our type I cluster showed the early systolic maximum and recognizable peak structure associated with TIBI grade 5 normal flow. In some arrangements, our type IV cluster exhibited the delayed flow acceleration with maximum velocity in mid-to-late systole characteristic of TIBI grade 2 blunted flow. In some arrangements, type I flows may be observed more often in control subjects. In some arrangements, type IV flows may more commonly be associated with LVO. In some arrangements, type II is more commonly observed in controls. In some arrangements, type III nearly always associated with LVO. In some arrangements, the pathological type III morphology may result from occlusion or stenosis of the cerebral vessels, though in a manner distinct from typically blunted waveforms, leaving the initial systolic acceleration unaffected while suppressing all subsequent morphological structure. In some arrangements the type II cluster, characterized by late onset maximal velocity but otherwise normal peaks, may reflect differences in peripheral vascular resistance relative to type I normal flow, which could conceivably impact either or both the initial systolic upstroke and/or the timing of reflected waves affecting the amplitude of the mid-systolic peak.

Considering the remaining TIBI flow grades, the lowest are not associated with sufficiently pulsatile CBFV waveforms, and thus could not be represented in our data set. Specifically, grade zero is defined as the absence of flow, whereas grade 1 (minimal flow) is so weakly pulsatile as to give rise to essentially flat waveforms when averaged over successive beats. The remaining TIBI flow grades 3 (Dampened), and 4 (Stenotic), are not solely morphologically defined, requiring comparison of velocity magnitude relative to a control waveform for their assignment, and thus cannot clearly align with our clusters. Future work could explore whether our clustering framework might be extended for application to sets of waveforms, including relative velocities as features, which might help reconstruct these latter TIBI categories.

In some arrangements, unsupervised learning may readily recover meaningful flow types bearing clear relation to known morphological categories. Moreover, the resultant cluster archetypes may ultimately serve as useful comparative templates, enabling automated categorization of TCD waveforms via minimal correlation distance. Future work will explore whether such labels can be combined with other metrics, such as VCI and velocity asymmetry, to improve LVO classification efficacy.

Although the method described herein has been shown in relation to TCD waveforms, the method can be used to cluster any type of waveforms, as desired.

Figure 8:
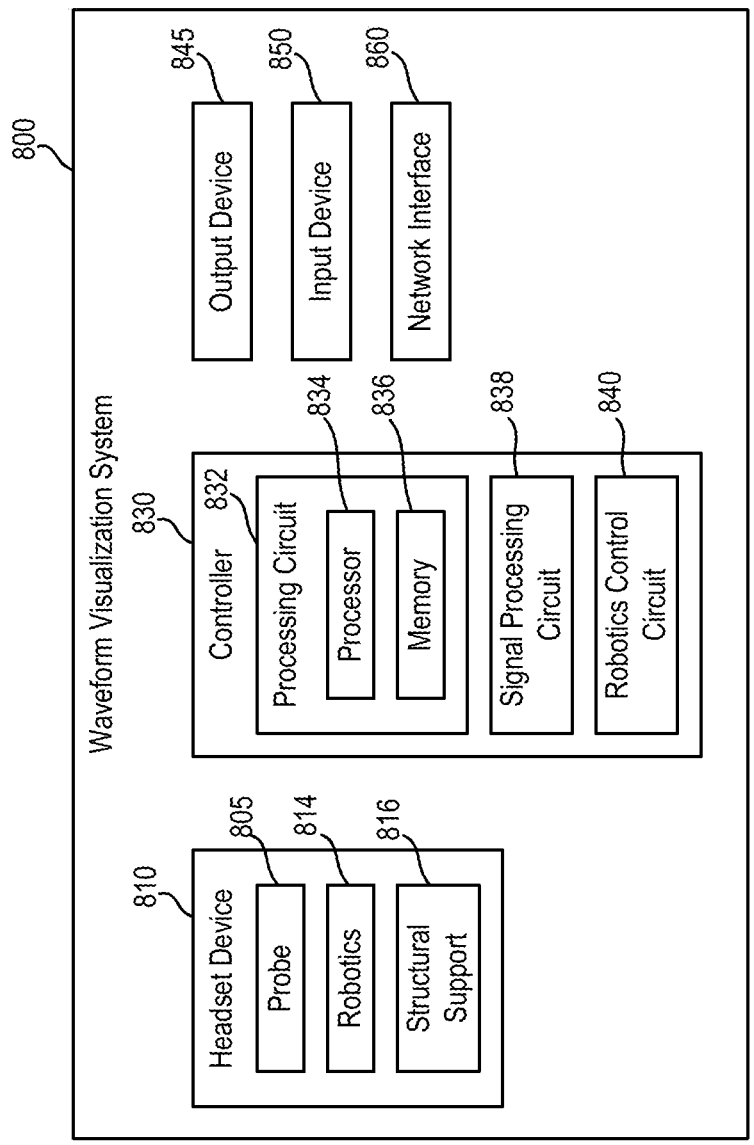
FIG. 8 is a schematic diagram illustrating a waveform visualization system 800 according to various arrangements.

FIG. 8 is a schematic diagram illustrating a waveform visualization system 800 according to various arrangements. Referring to FIGS. 1-8, the waveform visualization system 800 includes one or more of a headset device 810, a controller 830, an output device 845, an input device 850, and a network interface 860.

The headset device 810 is a TCD ultrasound device configured to emit and measure acoustic energy in a head of a patient. An example of the headset device 810 is a supine headset device. The headset device 810 includes at least one probe 805 (e.g., at least one ultrasound probe) configured to emit and measure ultrasound acoustic energy in the head. For example, the probe 805 includes at least one TCD scanner, which can automatically locate the middle cerebral artery (MCA) in some arrangements. At least one probe 805 can be positioned in a temporal window region (temple) of the head to collect the ultrasound data. In other arrangements, the probe can be positioned over different acoustic windows such as the transorbital window or the suboccipital window. In some arrangements, headset 810 includes two ultrasound probes 805, which can be placed on the temporal window region on both sides of the head. In some arrangements, the headset device 810 includes manually operated probes, as opposed to automatically or robotically-operated probes.

The controller 830 is configured to receive the ultrasound data outputted by the headset device 810 and to generate CBFV waveforms that correspond to the ultrasound data. In that regard, the probe 810 is operatively coupled to the controller 830 via a suitable network to send the ultrasound data to the controller 830. The network can be wired or wireless (e.g., 802.11X, ZigBee, Bluetooth®, Wi-Fi, or the like). The controller 830 can further perform signal processing functions to determine and display morphological indicators corresponding to the CBFV waveforms to facilitate a physician, clinician, technician, or care provider with diagnosis and/or to adjust the positioning of the headset device 810 and the probe 805. Further, as described, the headset device 810 can automatically adjust the position and orientation of the probe 805 responsive to determination that the probe 805 is not optimally placed based on the morphological indicators in the manner described herein. In some arrangements, the controller 830, the output device 845, and a portion of the network are incorporated into a single device (e.g., a touchscreen tablet device).

In some arrangements, the output device 845 includes any suitable device configured to display information, results, messages, and the like to an operator (e.g., a physician, clinician, technician, or care provider) of the waveform visualization system 800. For example, the output device 845 includes but is not limited to, a monitor, a touchscreen, or any other output device configured to display the CBFV waveforms, the morphology indicators, and the like for facilitating diagnosis and/or the positioning of the headset device 810 and the probe 805 relative to the head in the manner described.

In some arrangements, the headset device 810 includes robotics 814 configured to control positioning of the probe 805. For example, the robotics 814 are configured to translate the probe 805 along a surface of the head and to move the probe 805 with respect to (e.g., toward and away from) the head along various axes in the Cartesian, spherical, and rotational coordinate systems. In particular, the robotics 814 can include a multiple degree of freedom (DOF) TCD transducer positioning system with motion planning. In some embodiments, the robotics 814 are capable of supporting two, three, four, five, or six DOF movements of the probe 805 with respect to the head. In some instances, the robotics 814 can translate in X and Y axes (e.g., along a surface of the head) to locate a temporal window region in translational axes, and in Z axis with both force and position feedback control to both position, and maintain the appropriate force against the skull/skin to maximize signal quality by maintaining appropriate contact force. Two angular DOF (e.g., pan and tilt) may be used to maximize normal insonation of blood vessels to maximize velocity signals.

In some arrangements, an end of the probe 805 is operatively coupled to or otherwise interfaces with the robotics 814. The robotics 814 include components, such as but not limited to a motor assembly and the like for controlling the positioning of the probe 805 (e.g., controlling z-axis pressure, normal alignment, or the like of the probe 805). In some arrangements, the registration of the probe 805 against the head 805 is accomplished using the robotics 814 to properly position and align the probe 805 in the manner described.

In some arrangements, the probe 805 includes a first end and a second end that is opposite to the first end. In some arrangements, the first end includes a concave surface that is configured to be adjacent to or contact a scanning surface on the head. The concave surface is configured with a particular pitch to focus generated energy towards the scanning surface. In some arrangements, the headset device 810 is a TCD apparatus such that the first end of the probe 805 is configured to be adjacent to or contact and align along a side of the head. The first end of the probe 805 is configured to provide ultrasound wave emissions from the first end and directed into the head (e.g., toward the brain). For example, the first end of the probe 805 can include a transducer (such as, but not limited to, an ultrasound transducer, TCD, transcranial color-coded sonography (TCCS), or acoustic ultrasound transducer array such as sequential arrays or phased arrays) that emits acoustic energy capable of penetrating windows in the skull/head or neck. In other arrangements, the probe 805 is configured to emit other types of waves during operation, such as, but not limited to, infrared (IR), near-infrared spectroscopy (NIRS), electro-magnetic, x-rays, or the like.

In some arrangements, the second end of the probe 805 is coupled to the robotics 814. In some arrangements, the second end of the probe 805 includes a threaded section along a portion of the body of the probe 805. The second end is configured to be secured in the robotics 814 via the threads (e.g., by being screwed into the robotics 814). In other arrangements, the probe 805 is secured in the robotics 814 by any other suitable connecting means, such as but not limited to welding, adhesive, one or more hooks and latches, one or more separate screws, press fittings, or the like.

The headset device 810 can further include a structural support 816 configured to support the head of the patient and/or to support the headset device 810 on the head or other parts of a body of the patient. In some examples, the structural support 816 includes a platform (e.g., a baseplate) that allows the patient to lay down on a flat surface in a reclined or supine position while the headset device 810 is operational. In other examples, the structural support 816 includes one or more of a mount, cradle, headband, strap, Velcro®, hat, helmet, or another suitable wearable structure of the like such that the patient can wear the headset device 810 on the head, shoulders, neck, and/or the like when the patient is sitting, standing, or lying down. The structural support 816 can be made from any suitably malleable material that allows for flexing, such as, but not limited to, flexible plastics, polyethylene, urethanes, polypropylene, ABS, nylon, fiber-reinforced silicones, structural foams, or the like.

While the headset device 810 is shown and described as a headset such that the headset device 810 is lightweight and portable, one of ordinary skill in the art recognizes that the headset device 810 can be implemented with other types of TCD devices.

In some arrangements, the waveform visualization system 800 includes an input device 850. The input device 850 includes any suitable device configured to allow an operator, physician, or care provider personnel to input information or commands into the waveform visualization system 800. In some arrangements, the input device 850 includes but is not limited to, a keyboard, a keypad, a mouse, a joystick, a touchscreen display, or any other input device performing a similar function. In some arrangements, the input device 850 and the output device 845 can be a same input/output device (e.g., a touchscreen display device).

In some arrangements, the network interface 860 is structured for sending and receiving data (e.g., results, instructions, requests, software or firmware updates, and the like) over a communication network. Accordingly, the network interface 860 includes any of a cellular transceiver (for cellular standards), local wireless network transceiver (for 802.11X, ZigBee, Bluetooth®, Wi-Fi, or the like), wired network interface, a combination thereof (e.g., both a cellular transceiver and a Bluetooth transceiver), and/or the like. In some examples, the network interface 860 includes any method or device configured to send data from the headset device 810 to the controller 830. In that regard, the network interface 860 may include Universal Serial Bus (USB), FireWire, serial communication, and the like.

In some arrangements, the input device 850, the output device 845, the network interface 860, and the controller 830 form a single computing system that resides on a same node on the network, and the headset device 810 is connected to the computing system via the network, the network interface 860 is configured to communicate data to and from the headset device 810 via the network. In such arrangements, the headset device 810 includes a similar network interface (not shown) to communicate data to and from the computing device via the network. In other arrangements in which the headset device 810, the controller 830, the output device 845, the input device 850, and the network interface 860 all reside in a same computing device on a same node of a network, the network interface 860 is configured to communicate data with another suitable computing system (e.g., cloud data storage, remote server, and the like).

In some arrangements, the controller 830 is configured for controlling operations, processing data, executing input commands, providing results, and the like with respect to the waveform visualization system 800, and in particular, in relation to the morphology indicators as described herein. For example, the controller 830 is configured to receive input data or instructions from the input device 850 or the network interface 860, to control the waveform visualization system 800 to execute the commands, to receive data from the headset device 810, to provide information (e.g., the CBFV waveforms and the morphology indicators) to the output device 845 or network interface 860, and so on.

The controller 830 includes a processing circuit 832 having a processor 834 and a memory 836. In some arrangements, the processor 834 can be implemented as a general-purpose processor and is coupled to the memory 836. The processor 834 includes any suitable data processing device, such as a microprocessor. In the alternative, the processor 834 includes any suitable electronic processor, controller, microcontroller, or state machine. In some arrangements, the processor 834 is implemented as a combination of computing devices (e.g., a combination of a Digital Signal Processor (DSP) and a microprocessor, a plurality of microprocessors, at least one microprocessor in conjunction with a DSP core, or any other such configuration). In some arrangements, the processor 834 is implemented as an Application Specific Integrated Circuit (ASIC), one or more Field Programmable Gate Arrays (FPGAs), a Digital Signal Processor (DSP), a group of processing components, or other suitable electronic processing components.

In some arrangements, the memory 836 includes a non-transitory processor-readable storage medium that stores processor-executable instructions. In some arrangements, the memory 836 includes any suitable internal or external device for storing software and data. Examples of the memory 836 include but are not limited to, Random Access Memory (RAM), Read-Only Memory (ROM), Non-Volatile RAM (NVRAM), flash memory, floppy disks, hard disks, dongles or other Recomp Sensor Board (RSB)-connected memory devices, or the like. The memory 836 can store an Operating System (OS), user application software, and/or executable instructions. The memory 836 can also store application data, such as an array data structure. In some arrangements, the memory 836 stores data and/or computer code for facilitating the various processes described herein.

As used herein, the term "circuit" can include hardware structured to execute the functions described herein. In some arrangements, each respective circuit can include machine-readable media for configuring the hardware to execute the functions described herein. The circuit can be embodied as one or more circuitry components including, but not limited to, processing circuitry, network interfaces, peripheral devices, input devices, output devices, sensors, etc. In some arrangements, a circuit can take the form of one or more analog circuits, electronic circuits (e.g., integrated circuits (IC), discrete circuits, system on a chip (SOCs) circuits, etc.), telecommunication circuits, hybrid circuits, and any other suitable type of circuit. In this regard, the circuit can include any type of component for accomplishing or facilitating achievement of the operations described herein. For example, a circuit as described herein can include one or more transistors, logic gates (e.g., NAND, AND, NOR, OR, XOR, NOT, XNOR, etc.), resistors, multiplexers, registers, capacitors, inductors, diodes, wiring, and so on.

The circuit can also include one or more processors communicatively coupled to one or more memory or memory devices. In this regard, the one or more processors can execute instructions stored in the memory or can execute instructions otherwise accessible to the one or more processors. In some arrangements, the one or more processors can be embodied in various ways. The one or more processors can be constructed in a manner sufficient to perform at least the operations described herein. In some arrangements, the one or more processors can be shared by multiple circuits (e.g., a first circuit and a second circuit can include or otherwise share the same processor which, in some example arrangements, can execute instructions stored, or otherwise accessed, via different areas of memory). Alternatively, or additionally, the one or more processors can be structured to perform or otherwise execute certain operations independent of one or more co-processors. In other example arrangements, two or more processors can be coupled via a bus to enable independent, parallel, pipelined, or multi-threaded instruction execution. Each processor can be implemented as one or more general-purpose processors, ASICs, FPGAs, DSPs, or other suitable electronic data processing components structured to execute instructions provided by memory. The one or more processors can take the form of a single core processor, multi-core processor (e.g., a dual core processor, triple core processor, quad core processor, etc.), microprocessor, etc. In some arrangements, the one or more processors can be external to the apparatus, for example, the one or more processors can be a remote processor (e.g., a cloud-based processor). Alternatively, or additionally, the one or more processors can be internal and/or local to the apparatus. In this regard, a given circuit or components thereof can be disposed locally (e.g., as part of a local server, a local computing system, etc.) or remotely (e.g., as part of a remote server such as a cloud-based server). To that end, a circuit, as described herein can include components that are distributed across one or more locations.

The circuit can also include electronics for emitting and receiving acoustic energy such as a power amplifier, a receiver, a low noise amplifier or other transmitter receiver components. In some embodiments, the electronics are an ultrasound system. In some embodiments, the system includes a headset which is used to adjust the position of a probe such as a TCD ultrasound probe. The headset can be configured manually or use an automated robotic system to position the probe over a desired location on the head. The probe transmits and receives acoustic energy which is controlled by an electronic circuit. The electronic circuit has an analog circuit component such as a power amplifier which sends a signal to the probe. The probe than receives the signal which is amplified by an analog low noise amplifier either within the probe or in the analog circuit. Both the transmitted and received signals may be digitized by the circuit. In some embodiments, the send and receive chain may be made up of entirely digital components.

An example system for implementing the overall system or portions of the arrangements can include a general-purpose computer, including a processing unit, a system memory, and a system bus that couples various system components including the system memory to the processing unit. Each memory device can include non-transient volatile storage media, non-volatile storage media, non-transitory storage media (e.g., one or more volatile and/or non-volatile memories), etc. In some arrangements, the non-volatile media may take the form of ROM, flash memory (e.g., flash memory such as NAND, 3D NAND, NOR, 3D NOR, etc.), Electrically Erasable Programmable Read-Only Memory (EEPROM), Magnetoresistive Random Access Memory (MRAM), magnetic storage, hard discs, optical discs, etc. In other arrangements, the volatile storage media can take the form of RAM, Thyristor Random Access Memory (TRAM), Z-Capacitor Random Access Memory (ZRAM), etc. Combinations of the above are also included within the scope of machine-readable media. In this regard, machine-executable instructions include, for example, instructions and data which cause a general-purpose computer, special purpose computer, or special purpose processing machines to perform a certain function or group of functions. Each respective memory device can be operable to maintain or otherwise store information relating to the operations performed by one or more associated circuits, including processor instructions and related data (e.g., database components, object code components, script components, etc.), in accordance with the example arrangements described herein.

The controller 830 further includes a signal processing circuit 838, which can be implemented with the processing circuit 832 or another dedicated processing circuit. The signal processing circuit 838 receives the ultrasound data from the headset device 810 and generates the waveforms as described herein. The signal processing circuit 838 can further determine the morphology indicators for the CBFV waveforms or the average thereof. The signal processing circuit 838 can configure the output device 845 to display the CBFV waveforms, the average thereof, and the morphology indicators.

The controller 830 further includes a robotic control circuit 840, which can be implemented with the processing circuit 832 or another dedicated processing circuit. The robotic control circuit 840 is configured to control the robotics 814 based on the morphology of the CBFV waveforms during the operation of the visualization system 800 in the manner described. In particular, the robotic control circuit 840 is configured to control the positioning of the probe 805 using information regarding the morphology of the waveforms.

Figure 9:
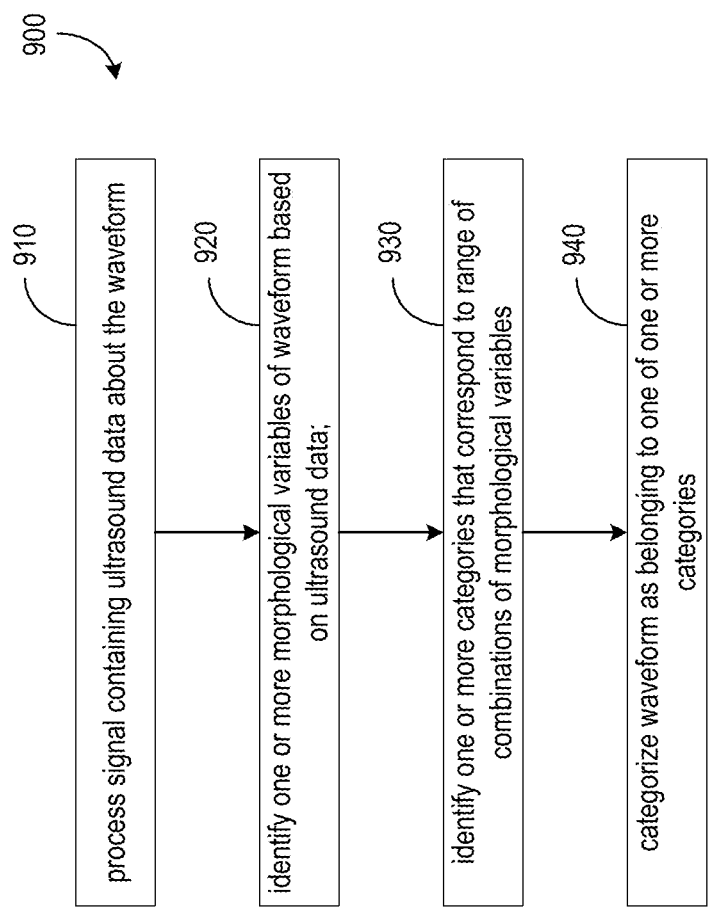
FIG. 9 is a method of categorizing a waveform, according to various arrangements.

FIG. 9 is a method 900 of categorizing a waveform, according to various arrangements. At 910, the waveform visualization system 800 processes a signal containing ultrasound data about the waveform. At 920, the waveform visualization system 800 identifies one or more morphological variables of the waveform based on the ultrasound data. At 930, the waveform visualization system 800 identifies one or more categories that correspond to a range of combinations of the morphological variables. At 940, the waveform visualization system 800 categorizes the waveform as belonging to one of the one or more categories.

In some arrangements, the method 900 further includes visualizing the one or more categories, for example, by displaying one or more of the diagrams of FIGS. 1-7. In some examples, categorizing the waveform as belonging to the one of the one or more categories includes determining a probability that the waveform belongs to the one or more categories and visualizing the one or more categories includes displaying the probability. In some examples, the one or more morphological variables include a first variable including an absolute peak onset of the waveform, a second variable including a length of a canopy of the waveform, and a third variable including one or more of a number of one or more auxiliary peaks of the waveform or prominence of the one or more auxiliary peaks of the waveform. In some examples, visualizing the one or more categories includes mapping the first variable along a first axis, the second variable along a second axis, and the third variable along a third axis. The first axis, the second axis, and the third axis are different axes. In some examples, each of the one or more categories corresponds to a designated area within a three-dimensional space defined by the first axis, the second axis, and the third axis.

In some examples, the first variable is categorized as early or late. The second variable is categorized as wide or narrow. The third variable is categorized as weak or strong.

In some examples, the waveform is categorized in the first category in response to determining that the first variable is categorized as late, the second variable is categorized as wide, and the third variable is categorized as strong. In some examples, the waveform is categorized in the second category in response to determining that the first variable is categorized as late, the second variable is categorized as wide, and the third variable is categorized as strong. In some examples, the waveform is categorized in the third category in response to determining that the first variable is categorized as early, the second variable is categorized as narrow, and the third variable is categorized as weak. In some examples, the waveform is categorized in the fourth category in response to determining that the first variable is categorized as late, the second variable is categorized as wide, and the third variable is categorized as weak.

In some examples, the waveform corresponds to blood flow within one or more cerebral arteries of the subject. The first category corresponds to the blood flow through the one or more cerebral arteries being normal. The third category corresponds to the blood flow through the one or more cerebral arteries being occluded. The fourth category corresponds to the blood flow through the one or more cerebral arteries being blunted. In some examples, the designated areas of two or more categories overlap.

In some examples, the waveform corresponds to blood flow of a subject. In some examples, the blood flow includes blood flow within one or more cerebral arteries of the subject. In some examples, the one or more categories correspond to one or more pathologies of the subject. In some examples, one of the one or more pathologies include one or more of stroke, intracranial hypertension, and mild traumatic brain injury. In some examples, the one or more categories include four categories that correspond to previously known TIBI flows. In some examples, a TCD transducer collects the ultrasound data and identifies the one or more morphological features of the waveform. In some examples, an automated algorithm is instructed to perform the method.

In some examples, the signal includes samples. Processing the signal containing ultrasound data includes determining the waveform based on the samples. The waveform being an representative waveform of the samples. The method further includes displaying the waveform and the samples (as shown in FIGS. 2, 3B-3E, and 6).

Figure 10:
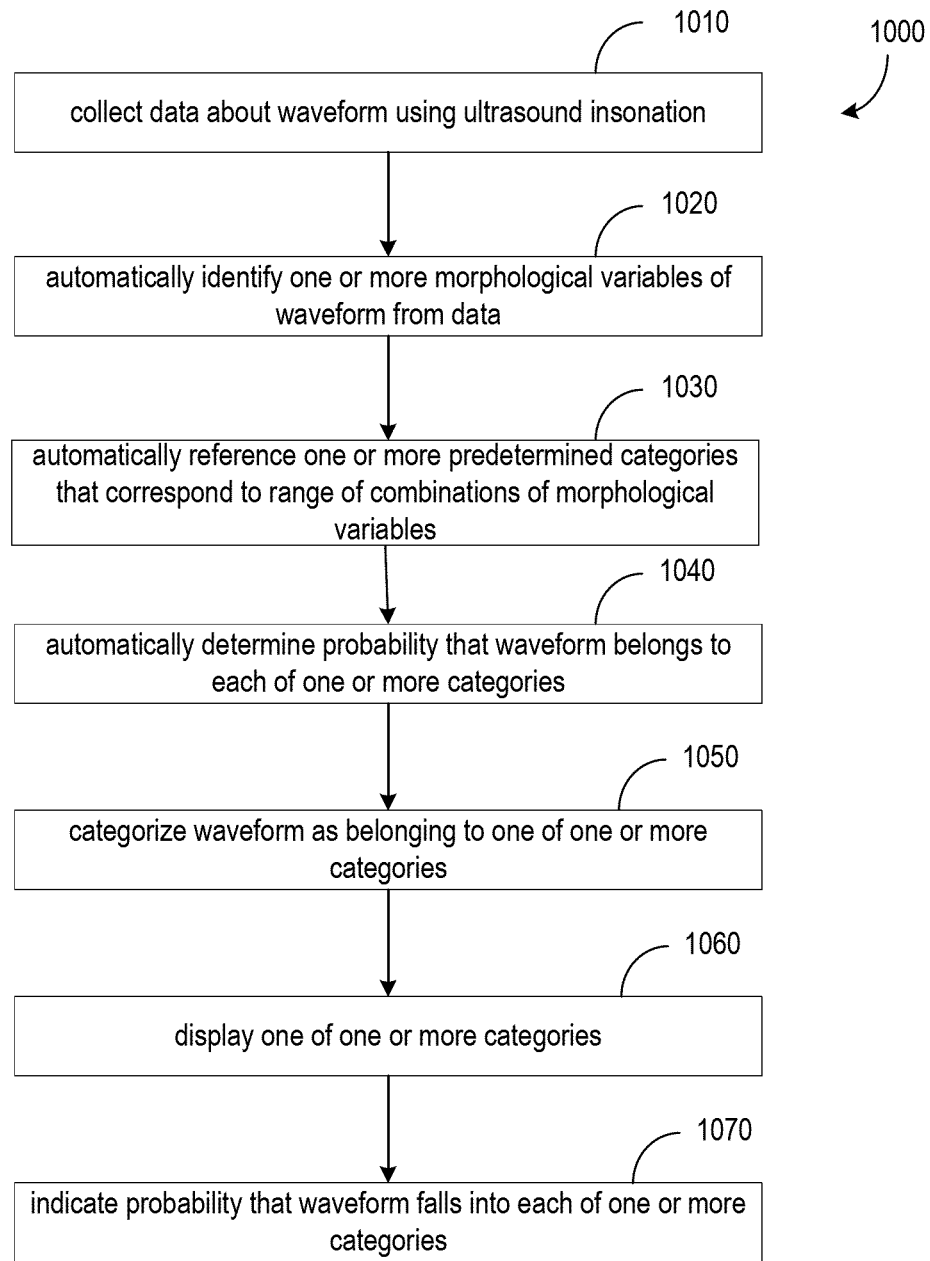
FIG. 10 is a method for visualizing characteristics a waveform, according to various arrangements.

FIG. 10 is a method 100 for visualizing a waveform, according to various arrangements. At 1010, the waveform visualization system 800 collects data about a waveform using ultrasound insonation. At 1020, the waveform visualization system 800 automatically identifies one or more morphological variables of the waveform from the data. At 1030, the waveform visualization system 800 automatically references one or more predetermined categories that correspond to a range of combinations of the morphological variables. At 1040, the waveform visualization system 800 automatically determine a probability that the waveform belongs to each of the one or more categories. At 1050, the waveform visualization system 800 categorizes the waveform as belonging to one of the one or more categories. At 1060, the waveform visualization system 800 displays the one of the one or more categories. At 1070, the waveform visualization system 800 indicates the probability that the waveform falls into each of the one or more categories.

In some examples, a first variable of the one or more morphological variables includes an absolute peak onset of the waveform. In some examples, a second variable of the one or more morphological variables includes a length of a canopy of the waveform. In some examples, a third variable of the one or more morphological variables includes one of a number or prominence of an auxiliary peak of the waveform.

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but is to be accorded the full scope consistent with the language claims, wherein reference to an element in the singular is not intended to mean "one and only one" unless specifically so stated, but rather "one or more." Unless specifically stated otherwise, the term "some" refers to one or more. All structural and functional equivalents to the elements of the various aspects described throughout the previous description that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

It is understood that the specific order or hierarchy of steps in the processes disclosed is an example of illustrative approaches. Based upon design preferences, it is understood that the specific order or hierarchy of steps in the processes may be rearranged while remaining within the scope of the previous description. The accompanying method claims present elements of the various steps in a sample order, and are not meant to be limited to the specific order or hierarchy presented.

The previous description of the disclosed implementations is provided to enable any person skilled in the art to make or use the disclosed subject matter. Various modifications to these implementations will be readily apparent to those skilled in the art, and the generic principles defined herein may be applied to other implementations without departing from the spirit or scope of the previous description. Thus, the previous description is not intended to be limited to the implementations shown herein but is to be accorded the widest scope consistent with the principles and novel features disclosed herein.

The various examples illustrated and described are provided merely as examples to illustrate various features of the claims. However, features shown and described with respect to any given example are not necessarily limited to the associated example and may be used or combined with other examples that are shown and described. Further, the claims are not intended to be limited by any one example.

The foregoing method descriptions and the process flow diagrams are provided merely as illustrative examples and are not intended to require or imply that the steps of various examples must be performed in the order presented. As will be appreciated by one of skill in the art the order of steps in the foregoing examples may be performed in any order. Words such as "thereafter," "then," "next," etc. are not intended to limit the order of the steps; these words are simply used to guide the reader through the description of the methods. Further, any reference to claim elements in the singular, for example, using the articles "a," "an" or "the" is not to be construed as limiting the element to the singular.

The various illustrative logical blocks, modules, circuits, and algorithm steps described in connection with the examples disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The hardware used to implement the various illustrative logics, logical blocks, modules, and circuits described in connection with the examples disclosed herein may be implemented or performed with a general purpose processor, a DSP, an ASIC, an FPGA or other programmable logic device, discrete gate or transistor logic, discrete hardware components, or any combination thereof designed to perform the functions described herein. A general-purpose processor may be a microprocessor, but, in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. Alternatively, some steps or methods may be performed by circuitry that is specific to a given function.

In some exemplary examples, the functions described may be implemented in hardware, software, firmware, or any combination thereof. If implemented in software, the functions may be stored as one or more instructions or code on a non-transitory computer-readable storage medium or non-transitory processor-readable storage medium. The steps of a method or algorithm disclosed herein may be embodied in a processor-executable software module which may reside on a non-transitory computer-readable or processor-readable storage medium. Non-transitory computer-readable or processor-readable storage media may be any storage media that may be accessed by a computer or a processor. By way of example but not limitation, such non-transitory computer-readable or processor-readable storage media may include RAM, ROM, EEPROM, FLASH memory, CD-ROM or other optical disk storage, magnetic disk storage or other magnetic storage devices, or any other medium that may be used to store desired program code in the form of instructions or data structures and that may be accessed by a computer. Disk and disc, as used herein, includes compact disc (CD), laser disc, optical disc, digital versatile disc (DVD), floppy disk, and blu-ray disc where disks usually reproduce data magnetically, while discs reproduce data optically with lasers. Combinations of the above are also included within the scope of non-transitory computer-readable and processor-readable media. Additionally, the operations of a method or algorithm may reside as one or any combination or set of codes and/or instructions on a non-transitory processor-readable storage medium and/or computer-readable storage medium, which may be incorporated into a computer program product.

The preceding description of the disclosed examples is provided to enable any person skilled in the art to make or use the present disclosure. Various modifications to these examples will be readily apparent to those skilled in the art, and the generic principles defined herein may be applied to some examples without departing from the spirit or scope of the disclosure. Thus, the present disclosure is not intended to be limited to the examples shown herein but is to be accorded the widest scope consistent with the following claims and the principles and novel features disclosed herein.

The invention claimed is:

1. A method of categorizing a waveform corresponding to a type of blood flow within one or more cerebral arteries of a subject, comprising:
   generating the waveform corresponding to ultrasound data by processing a signal containing the ultrasound data;
   identifying three morphological variables of the waveform based on the ultrasound data, wherein the three morphological variables comprise: a first variable comprising an absolute peak onset of the waveform, a second variable comprising a length of a canopy of the waveform, and a third variable comprising one or more of a number of one or more auxiliary peaks of the waveform or prominence of the one or more auxiliary peaks of the waveform;
   mapping the three morphological variables to a three-dimensional space defined by three axes, wherein each of the three morphological variables corresponds to one of the three axes;
   identifying two or more categories that correspond to a range of combinations of the morphological variables based on the three-dimensional space;
   determining a probability that the waveform belongs to the two or more categories;
   categorizing the waveform as belonging to one of the two or more categories;
   visualizing the two or more categories; and
   displaying the probability that the waveform belongs to the two or more categories.

2. The method of claim 1, wherein visualizing the two or more categories comprises mapping: the first variable along a first axis; the second variable along a second axis; and the third variable along a third axis, wherein the first axis, the second axis, and the third axis are different axes.

3. The method of claim 2, wherein each of the two or more categories corresponds to a designated area within the three-dimensional space defined by the first axis, the second axis, and the third axis.

4. The method of claim 1, wherein: the first variable is categorized as early or late; the second variable is categorized as wide or narrow; and the third variable is categorized as weak or strong.

5. The method of claim 4, wherein the waveform is categorized in:
   the first category in response to determining that the first variable is categorized as early, the second variable is categorized as wide, and the third variable is categorized as strong;
   the second category in response to determining that the first variable is categorized as late, the second variable is categorized as wide, and the third variable is categorized as strong;
   the third category in response to determining that the first variable is categorized as early, the second variable is categorized as narrow, and the third variable is categorized as weak; and
   the fourth category in response to determining that the first variable is categorized as late, the second variable is categorized as wide, and the third variable is categorized as weak.

6. The method of claim 5, wherein:
   the first category corresponds to the blood flow through the one or more cerebral arteries being normal;
   the third category corresponds to the blood flow through the one or more cerebral arteries being occluded; and
   the fourth category corresponds to the blood flow through the one or more cerebral arteries being blunted.

7. The method of claim 6, wherein the designated areas of two or more categories overlap.

8. The method of claim 1, wherein the two or more categories correspond to one or more pathologies of the subject.

9. The method of claim 8, wherein one of the one or more pathologies comprise one or more of stroke, intracranial hypertension, and mild traumatic brain injury.

10. The method of claim 1, wherein the two or more categories comprise four categories that correspond to previously known Thrombolysis in Brain Ischemia (TIM) flows.

11. The method of claim 1 wherein a Transcranial Doppler (TCD) transducer collects the ultrasound data and identifies the three morphological features of the waveform.

12. The method of claim 1, wherein an automated algorithm is instructed to perform the method.

13. The method of claim 1, wherein
   the signal comprises samples;
   processing the signal containing ultrasound data comprises determining the waveform based on the samples, the waveform being an representative waveform of the samples; and
   the method further comprises displaying the waveform and the samples.

14. A method of visualizing waveforms corresponding to a type of blood flow within one or more cerebral arteries of a subject, comprising:
   collecting data about a waveform using ultrasound insonation;
   automatically identifying three morphological variables of the waveform from the data, wherein the three morphological variables comprise: a first variable comprising an absolute peak onset of the waveform, a second variable comprising a length of a canopy of the waveform, and a third variable comprising one or more of a number of one or more auxiliary peaks of the waveform or prominence of the one or more auxiliary peaks of the waveform;
   mapping the three morphological variables to a three-dimensional space defined by three axes, wherein each of the three morphological variables corresponds to one of the three axes;
   automatically referencing two or more predetermined categories that correspond to a range of combinations of the morphological variables based on the three-dimensional space;
   automatically determining a probability that the waveform belongs to each of the two or more categories;
   categorizing the waveform as belonging to one of the two or more categories;
   displaying the one of the two or more categories; and
   indicating the probability that the waveform falls into each of the two or more categories.

15. A device for visualizing categorization of a waveform corresponding to a type of blood flow within one or more cerebral arteries of a subject, wherein the device comprises:
- a probe configured to collect data from the waveform;
- a processing circuit configured to:
  - identify three morphological variables of the waveform from the data, wherein the three morphological variables comprise: a first variable comprising an absolute peak onset of the waveform, a second variable comprising a length of a canopy of the waveform, and a third variable comprising one or more of a number of one or more auxiliary peaks of the waveform or prominence of the one or more auxiliary peaks of the waveform;
  - map the three morphological variables to a three-dimensional space defined by three axes, wherein each of the three morphological variables corresponds to one of the three axes;
  - reference two or more predetermined categories that correspond to a range of combinations of the morphological variables based on the three-dimensional space;
  - determine a probability that the waveform belongs to each of the two or more predetermined categories; and
  - categorize the waveform as belonging to one of the two or more predetermined categories; and
- an output device, wherein the output device displays the one of the two or more predetermined categories and the probability determined by the processing circuit.

* * * * *